US008556831B1

(12) United States Patent
Faber et al.

(10) Patent No.: US 8,556,831 B1
(45) Date of Patent: Oct. 15, 2013

(54) BODY TRAUMA ANALYSIS METHOD AND APPARATUS

(76) Inventors: Robert Branch Faber, Nashville, TN (US); Ataullah Arjomand, Bellevue, WA (US)

(*) Notice: Subject to any disclaimer, the term of this patent is extended or adjusted under 35 U.S.C. 154(b) by 0 days.

(21) Appl. No.: 13/604,459

(22) Filed: Sep. 5, 2012

(51) Int. Cl.
*A61B 5/103* (2006.01)
*A61B 5/117* (2006.01)
*G08B 1/08* (2006.01)
*G08B 21/00* (2006.01)

(52) U.S. Cl.
USPC ........... 600/587; 600/595; 340/500; 340/501; 340/539.11; 340/539.12; 340/669

(58) Field of Classification Search
None
See application file for complete search history.

(56) References Cited

U.S. PATENT DOCUMENTS

| | | | |
|---|---|---|---|
| 2002/0116080 A1* | 8/2002 | Birnbach et al. | 700/66 |
| 2005/0177335 A1* | 8/2005 | Crisco et al. | 702/141 |
| 2005/0177929 A1* | 8/2005 | Greenwald et al. | 2/425 |
| 2011/0181419 A1* | 7/2011 | Mack et al. | 340/573.1 |
| 2011/0181420 A1* | 7/2011 | Mack et al. | 340/573.1 |
| 2011/0205077 A1* | 8/2011 | Cavallaro et al. | 340/686.6 |
| 2011/0273286 A1* | 11/2011 | Sklar | 340/539.12 |
| 2012/0077440 A1* | 3/2012 | Howard et al. | 455/41.2 |
| 2012/0147009 A1* | 6/2012 | Benzel et al. | 345/440 |
| 2012/0150453 A1* | 6/2012 | Benzel et al. | 702/41 |
| 2012/0174302 A1* | 7/2012 | Jenkins, III | 2/468 |
| 2012/0188083 A1* | 7/2012 | Miller, II | 340/573.1 |
| 2012/0306642 A1* | 12/2012 | Howard et al. | 340/539.11 |
| 2012/0309300 A1* | 12/2012 | Howard et al. | 455/39 |

* cited by examiner

*Primary Examiner* — Brian Szmal
*Assistant Examiner* — Megan Leedy
(74) *Attorney, Agent, or Firm* — Arjomand Law Group, PLLC

(57) ABSTRACT

A method and a device are disclosed including a clothing article with an embedded Data Measurement and Processing Module configured to measure a dynamic characteristic of a predefined significant impact to the user of the clothing article, and further including a video capturing device which provides video scenes related to the impact. In various embodiments, the embedded data collection and measurement module includes a multi-axis accelerometer and a processor, such as a microcontroller, coupled with the accelerometer to calculate a magnitude and direction of the imparted force, and a video camera that is configured to relate its different captured scenes to predefined significant impacts within each scene. In other various embodiments, the processor and/or the video capturing device may communicate collected and/or calculated data to a storage device and/or an external host computer for future analysis and use.

20 Claims, 6 Drawing Sheets

BODY TRAUMA ANALYSIS METHOD AND APPARATUS

CROSS-REFERENCE TO RELATED U.S. APPLICATIONS

This application is related to U.S. patent application Ser. No. 13/604,104, filed on Sep. 5, 2012.

TECHNICAL FIELD

This application relates generally to health and safety. More specifically, this application relates to a system and method for investigating characteristics of an impact to a person's body as a result of an impact or explosion.

BRIEF DESCRIPTION OF THE DRAWINGS

The drawings, when considered in connection with the following description, are presented for the purpose of facilitating an understanding of the subject matter sought to be protected.

DETAILED DESCRIPTION

Figure 1:
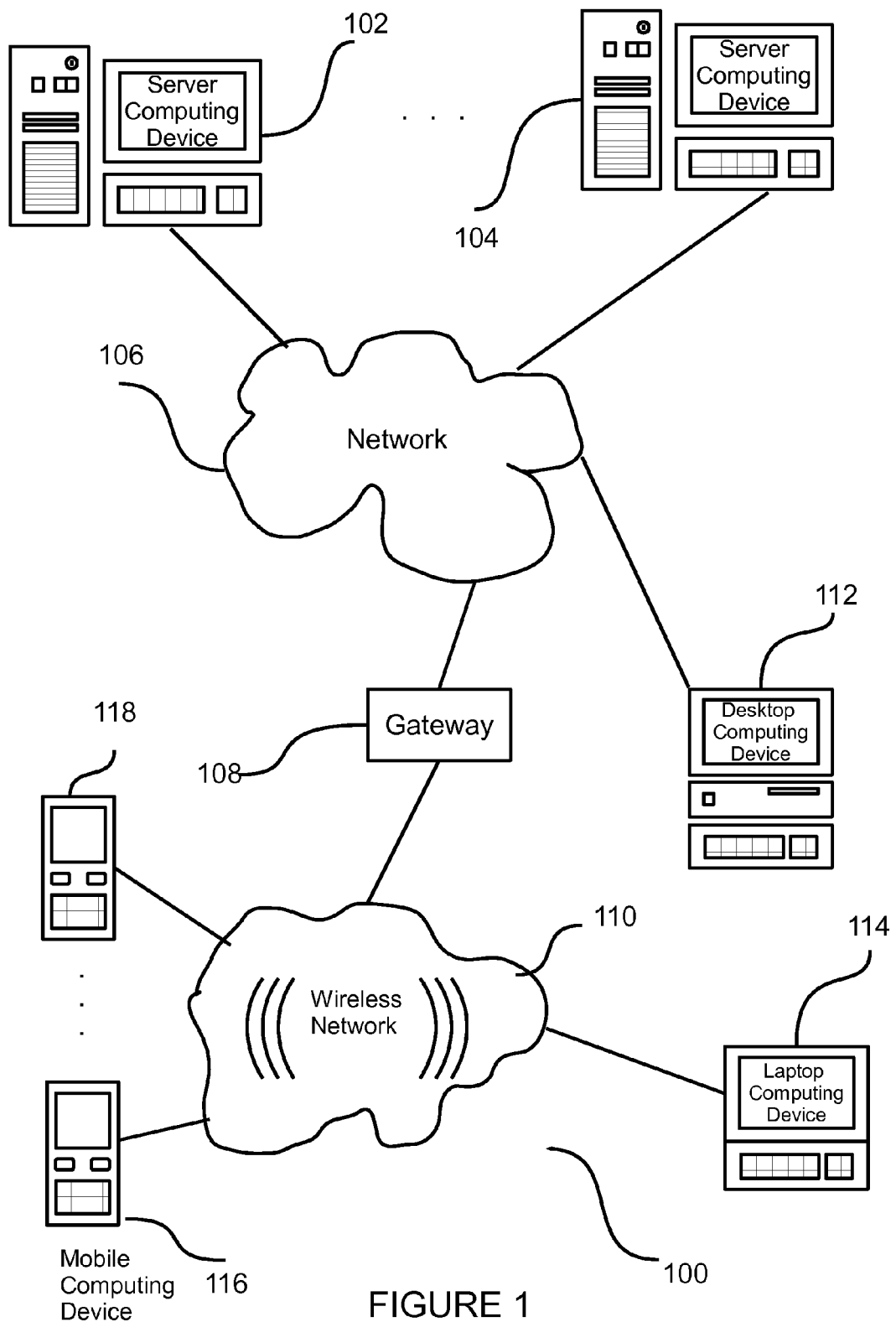
FIG. 1 shows an embodiment of a network computing environment wherein the disclosure may be practiced.

While the present disclosure is described with reference to several illustrative embodiments explained herein, it should be clear that the present disclosure should not be limited to such embodiments. Therefore, the description of the embodiments provided herein is illustrative of the present disclosure and should not limit the scope of the disclosure as claimed. In addition, while following description references particular types of helmets, headbands, and in general "headgears", and sports such as American football and Karate, it will be appreciated that the disclosure may be used with other types of sports and other gear and clothing articles and activities such as those associated with military, police and rescue personnel, riot police, and the like.

Many activities and sports, such as falls, being near explosions, American football, hockey, boxing, martial arts, and the like, include abrupt physical contact which may sometimes cause concussion also known as Mild Traumatic Brain Injury ("MTBI"), or other trauma, to a player. For example, in American football players are often tackled at relatively high running speeds creating significant physical impacts on the players' bodies and heads, which may result in some level of concussion or trauma. There are medical data which indicate concussion may result not only from one or a few hard blows, but also from repeated softer impacts over time causing cumulative micro injuries to the brain. As such, it is desirable to track the number and severity of blows received by a player or participant in impact activities, such as athletes, police, and soldiers. It is also desirable to raise an alarm if a blow is too hard and may have caused a more severe trauma or may do so if repeated. It is also desirable, for example for training purposes, to be able to watch the exact scene in which a particular impact has occurred. The disclosed apparatus and methods can also be used for instruction purposes.

Briefly described, a device and a method are disclosed including a clothing article such as a sport gear or helmet with an embedded Data Measurement and Processing Module ("DMPM") configured to at least measure one of the out-of-bound, with respect to a predefined boundary, or otherwise significant characteristics or attributes of an impact, such as speed, acceleration, force, energy, or momentum imparted on a user's body part due to impact or explosion, and further including a video capturing device, the captured images of which are closely associated and correlated with the measured impacts.

The gear or clothing article may also be further configured to provide a visual, an audible or other indication of a predetermined level of force, or of other predetermined dynamic and other characteristics, imparted on a user's body part. In various embodiments, the embedded data collection and measurement module includes an accelerometer, preferably a multi-axis accelerometer, and a processor, such as a microcontroller, coupled with the accelerometer to calculate a magnitude and direction of the imparted force or merely the direction and magnitude of the acceleration resulting from the imparted force to the head or body of the user. The processor may further provide an indicator such as a light or a sound to indicate that a predetermined acceleration and/or force threshold has been exceeded. In other various embodiments, the apparatus may communicate collected and/or calculated data to a storage device and/or an external host computer for future analysis and use.

Figure 3A:
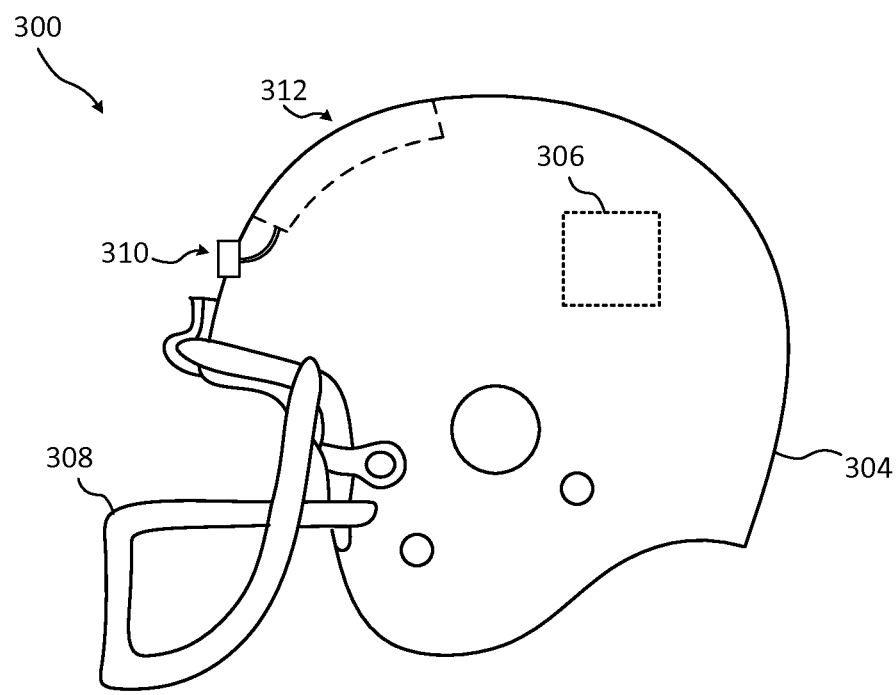
FIG. 3A shows an example sports helmet including a video capturing device and a data measurement and processing module configured to measure and capture an impact to a person's body.
Figure 4A:
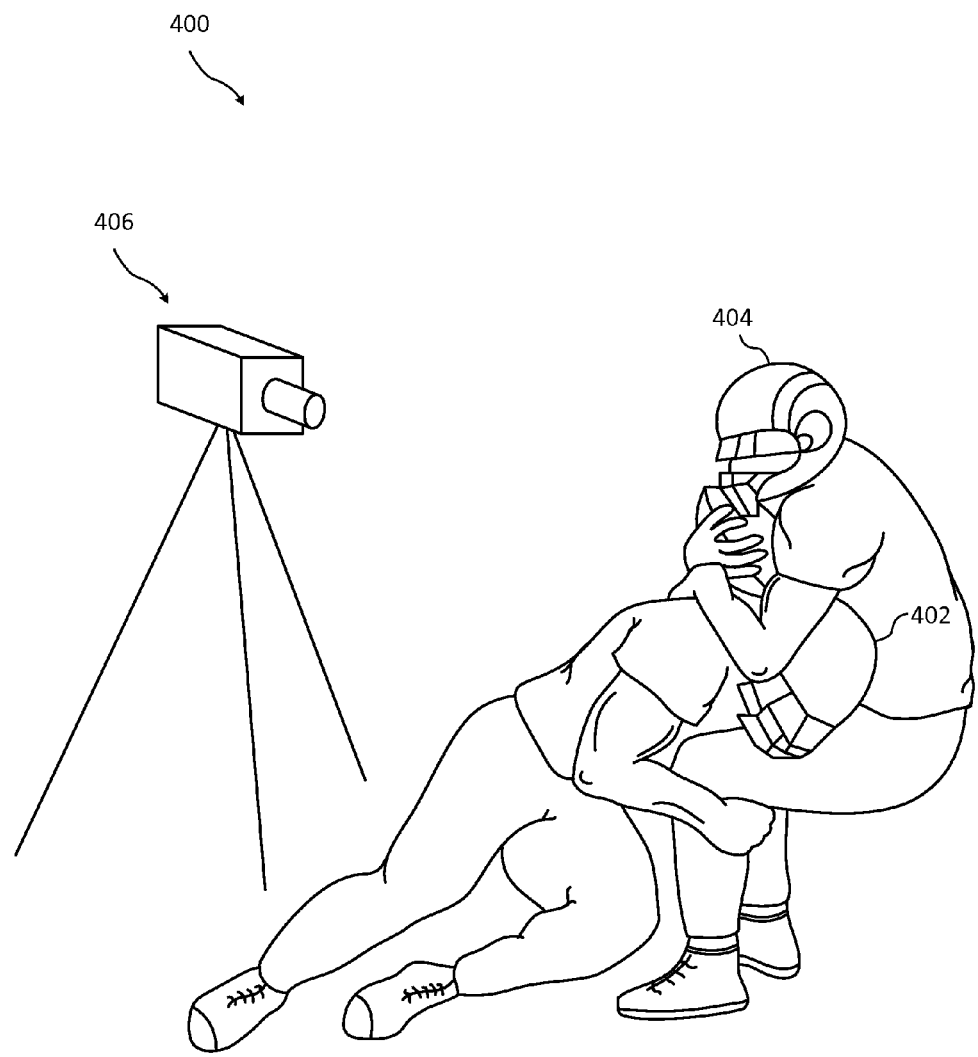
FIG. 4A shows an example American football encounter which may result in concussion.
Figure 4B:
FIG. 4B shows an example martial art encounter which may result in concussion.

As seen in FIGS. 3A, 4A, and 4B, in some embodiments the video capturing device is either a part of the user's clothing article and gear that includes the DMPM or is completely separate from the user, while in other embodiments the video capturing device is carried by the user or is worn by the user as a separate gear. It should be noted that in the following detailed description, wherever the visual aspects of a scene are intended the word "video" is used. Also, a "camera", a "video camera", or a "video capturing device" may produce a motion picture, a still picture, or both.

Illustrative Operating Environment

FIG. 1 shows components of an illustrative environment in which the disclosure may be practiced. Not all the shown components may be required to practice the disclosure, and variations in the arrangement and type of the components may be made without departing from the spirit or scope of the disclosure. System 100 may include Local Area Networks (LAN) and Wide Area Networks (WAN) shown collectively as Network 106, wireless network 110, gateway 108 configured to connect remote and/or different types of networks together, client computing devices 112-118, and server computing devices 102-104.

One embodiment of a computing device usable as one of client computing devices 112-118 is described in more detail below with respect to FIG. 2. Briefly, however, client computing devices 112-118 may include virtually any device capable of receiving and sending a message over a network, such as wireless network 110, or the like. Such devices include portable devices such as, cellular telephones, smart phones, digital cameras, display pagers, radio frequency (RF) devices, music players, digital cameras, infrared (IR) devices, Personal Digital Assistants (PDAs), handheld computers, laptop computers, wearable computers, tablet computers, integrated devices combining one or more of the preceding devices, and the like. Client device 112 may include virtually any computing device that typically connects using a wired communications medium such as personal computers, multiprocessor systems, microprocessor-based or programmable consumer electronics, network PCs, or the like. In one embodiment, one or more of client devices 112-118 may also be configured to operate over a wired and/or a wireless network.

Client devices 112-118 typically range widely in terms of capabilities and features. For example, a cell phone may have a numeric keypad and a few lines of monochrome LCD display on which only text may be displayed. In another example, a web-enabled client device may have a touch sensitive screen, a stylus, and several lines of color LCD display in which both text and graphic may be displayed.

A web-enabled client device may include a browser application that is configured to receive and to send web pages, web-based messages, or the like. The browser application may be configured to receive and display graphic, text, multimedia, or the like, employing virtually any web based language, including a wireless application protocol messages (WAP), or the like. In one embodiment, the browser application may be enabled to employ one or more of Handheld Device Markup Language (HDML), Wireless Markup Language (WML), WMLScript, JavaScript, Standard Generalized Markup Language (SMGL), HyperText Markup Language (HTML), eXtensible Markup Language (XML), or the like, to display and send information.

Client computing devices 12-118 also may include at least one other client application that is configured to receive content from another computing device, including, without limit, server computing devices 102-104. The client application may include a capability to provide and receive textual content, multimedia information, or the like. The client application may further provide information that identifies itself, including a type, capability, name, or the like. In one embodiment, client devices 112-118 may uniquely identify themselves through any of a variety of mechanisms, including a phone number, Mobile Identification Number (MIN), an electronic serial number (ESN), mobile device identifier, network address, such as IP (Internet Protocol) address, Media Access Control (MAC) layer identifier, or other identifier. The identifier may be provided in a message, or the like, sent to another computing device.

Client computing devices 112-118 may also be configured to communicate a message, such as through email, Short Message Service (SMS), Multimedia Message Service (MMS), instant messaging (IM), internet relay chat (IRC), Mardam-Bey's IRC (mIRC), Jabber, or the like, to another computing device. However, the present disclosure is not limited to these message protocols, and virtually any other message protocol may be employed.

Client devices 112-118 may further be configured to include a client application that enables the user to log into a user account that may be managed by another computing device. Such user account, for example, may be configured to enable the user to receive emails, send/receive IM messages, SMS messages, access selected web pages, download scripts, applications, or a variety of other content, or perform a variety of other actions over a network. However, managing of messages or otherwise accessing and/or downloading content, may also be performed without logging into the user account. Thus, a user of client devices 112-118 may employ any of a variety of client applications to access content, read web pages, receive/send messages, or the like. In one embodiment, for example, the user may employ a browser or other client application to access a web page hosted by a Web server implemented as server computing device 102. In one embodiment, messages received by client computing devices 112-118 may be saved in non-volatile memory, such as flash and/or PCM, across communication sessions and/or between power cycles of client computing devices 112-118.

Wireless network 110 may be configured to couple client devices 114-118 to network 106. Wireless network 110 may include any of a variety of wireless sub-networks that may further overlay stand-alone ad-hoc networks, and the like, to provide an infrastructure-oriented connection for client devices 114-118. Such sub-networks may include mesh networks, Wireless LAN (WLAN) networks, cellular networks, and the like. Wireless network 110 may further include an autonomous system of terminals, gateways, routers, and the like connected by wireless radio links, and the like. These connectors may be configured to move freely and randomly and organize themselves arbitrarily, such that the topology of wireless network 110 may change rapidly.

Wireless network 110 may further employ a plurality of access technologies including 2nd (2G), 3rd (3G), $4^{th}$ (4G), generation and any future generation technologies for radio access for cellular systems, WLAN, Wireless Router (WR) mesh, and the like. Access technologies such as 3G, 4G, and future access networks may enable wide area coverage for mobile devices, such as client devices 114-118 with various degrees of mobility. For example, wireless network 110 may enable a radio connection through a radio network access such as Global System for Mobil communication (GSM), General Packet Radio Services (GPRS), Enhanced Data GSM Environment (EDGE), WEDGE, Bluetooth, High Speed Downlink Packet Access (HSDPA), Universal Mobile Telecommunications System (UMTS), Wi-Fi, Zigbee, Wideband Code Division Multiple Access (WCDMA), and the like. In essence, wireless network 110 may include virtually any wireless communication mechanism by which information may travel between client devices 102-104 and another computing device, network, and the like.

Network 106 is configured to couple one or more servers depicted in FIG. 1 as server computing devices 102-104 and their respective components with other computing devices, such as client device 112, and through wireless network 110 to client devices 114-118. Network 106 is enabled to employ any form of computer readable media for communicating information from one electronic device to another. Also, network 106 may include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another.

Communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, remote computers and other related electronic devices could be remotely connected to either LANs or WANs via a modem and temporary telephone link. Network 106 may include any communication method by which information may travel between computing devices. Additionally, communication media typically may enable transmission of computer-readable instructions, data structures, program modules, or other types of content, virtually without limit. By way of example, communication media includes wired media such as twisted pair, coaxial cable, fiber optics, wave guides, and other wired media and wireless media such as acoustic, RF, infrared, and other wireless media.

Illustrative Computing Device Configuration

Figure 2:
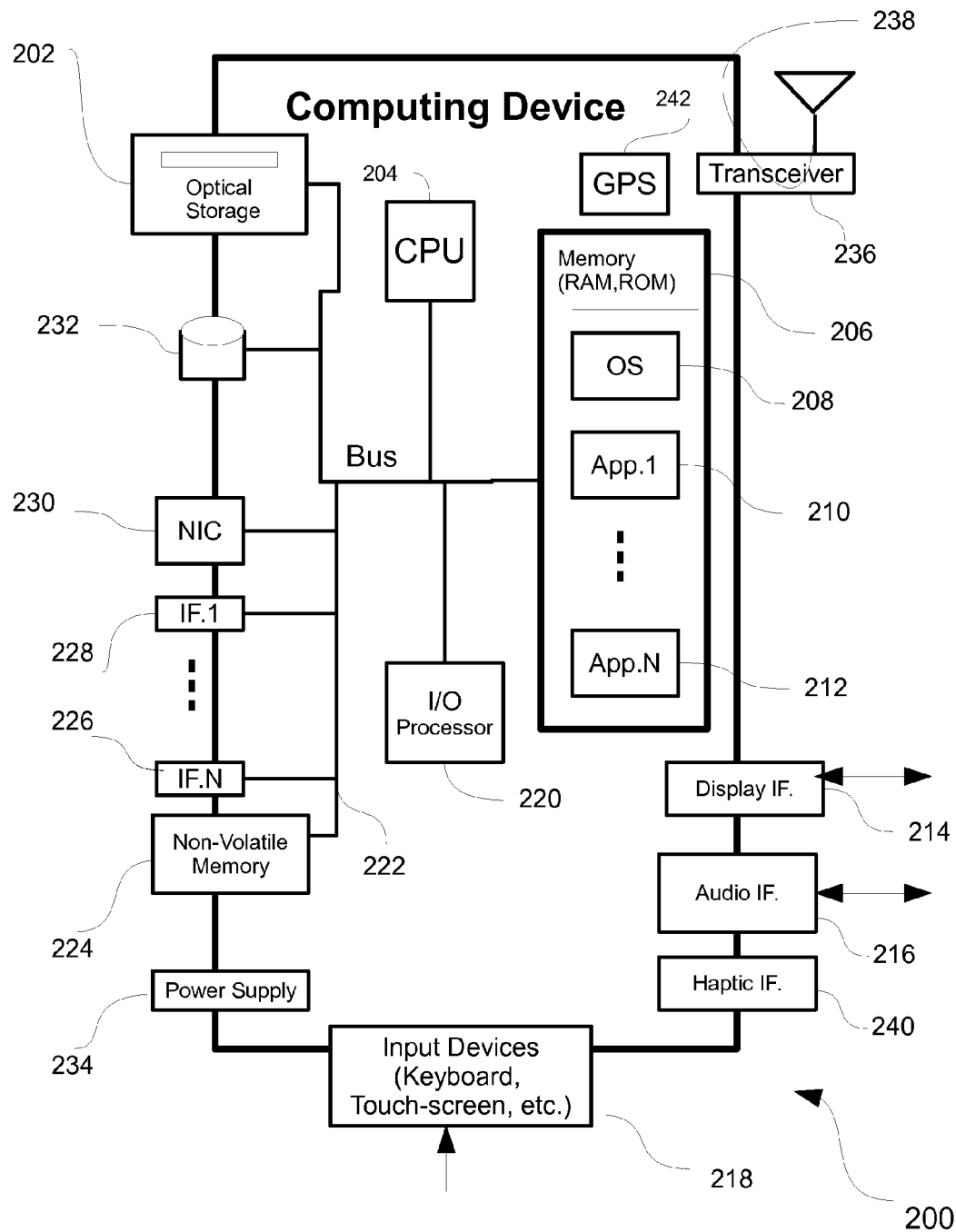
FIG. 2 shows an embodiment of a computing device that may be used in the network computing environment of FIG. 1.

FIG. 2 shows an illustrative computing device 200 that may represent any one of the server and/or client computing devices shown in FIG. 1. A computing device represented by computing device 200 may include less or more than all the components shown in FIG. 2 depending on the functionality needed. For example, a mobile computing device may include the transceiver 236 and antenna 238, while a server computing device 102 of FIG. 1 may not include these components. Those skilled in the art will appreciate that the scope of integration of components of computing device 200 may be different from what is shown. As such, some of the components of computing device 200 shown in FIG. 2 may be integrated together as one unit. For example, NIC 230 and transceiver 236 may be implemented as an integrated unit. Additionally, different functions of a single component may be separated and implemented across several components instead. For example, different functions of I/O processor 220 may be separated into two or more processing units.

With continued reference to FIG. 2, computing device 200 includes optical storage 202, Central Processing Unit (CPU) 204, memory module 206, display interface 214, audio interface 216, input devices 218, Input/Output (I/O) processor 220, bus 222, non-volatile memory 224, various other interfaces 226-228, Network Interface Card (NIC) 320, hard disk 232, power supply 234, transceiver 236, antenna 238, haptic interface 240, and Global Positioning System (GPS) unit 242. Memory module 206 may include software such as Operating System (OS) 208, and a variety of software application programs 210-212. Computing device 200 may also include other components not shown in FIG. 2. For example, computing device 200 may further include an illuminator (for example, a light), graphic interface, and portable storage media such as USB drives. Computing device 200 may also include other processing units, such as a math co-processor, graphics processor/accelerator, and a Digital Signal Processor (DSP).

Optical storage device 202 may include optical drives for using optical media, such as CD (Compact Disc), DVD (Digital Video Disc), and the like. Optical storage devices 202 may provide inexpensive ways for storing information for archival and/or distribution purposes.

Central Processing Unit (CPU) 204 may be the main processor for software program execution in computing device 200. CPU 204 may represent one or more processing units that obtain software instructions from memory module 206 and execute such instructions to carry out computations and/or transfer data between various sources and destinations of data, such as hard disk 232, I/O processor 220, display interface 214, input devices 218, non-volatile memory 224, and the like.

Memory module 206 may include RAM (Random Access Memory), ROM (Read Only Memory), and other storage means, mapped to one addressable memory space. Memory module 206 illustrates one of many types of computer storage media for storage of information such as computer readable instructions, data structures, program modules or other data. Memory module 206 may store a basic input/output system (BIOS) for controlling low-level operation of computing device 200. Memory module 206 may also store OS 208 for controlling the general operation of computing device 200. It will be appreciated that OS 208 may include a general-purpose operating system such as a version of UNIX, or LINUX™, or a specialized client communication operating system such as Windows Mobile™, or the Symbian® operating system. OS 208 may, in turn, include or interface with a Java virtual machine (JVM) module that enables control of hardware components and/or operating system operations via Java application programs.

Memory module 206 may further include one or more distinct areas (by address space and/or other means), which can be utilized by computing device 200 to store, among other things, applications and/or other data. For example, one area of memory module 206 may be set aside and employed to store information that describes various capabilities of computing device 200, a device identifier, and the like. Such identification information may then be provided to another device based on any of a variety of events, including being sent as part of a header during a communication, sent upon request, or the like. One common software application is a browser program that is generally used to send/receive information to/from a web server. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message. However, any of a variety of other web based languages may also be employed. In one embodiment, using the browser application, a user may view an article or other content on a web page with one or more highlighted portions as target objects.

Display interface 214 may be coupled with a display unit (not shown), such as liquid crystal display (LCD), gas plasma, light emitting diode (LED), or any other type of display unit that may be used with computing device 200. Display units coupled with display interface 214 may also include a touch sensitive screen arranged to receive input from an object such as a stylus or a digit from a human hand. Display interface 214 may further include interface for other visual status indicators, such Light Emitting Diodes (LED), light arrays, and the like. Display interface 214 may include both hardware and software components. For example, display interface 214 may include a graphic accelerator for rendering graphic-intensive outputs on the display unit. In one embodiment, display interface 214 may include software and/or firmware components that work in conjunction with CPU 204 to render graphic output on the display unit.

Audio interface 216 is arranged to produce and receive audio signals such as the sound of a human voice. For example, audio interface 216 may be coupled to a speaker and microphone (not shown) to enable communication with a human operator, such as spoken commands, and/or generate an audio acknowledgement for some action.

Input devices 218 may include a variety of device types arranged to receive input from a user, such as a keyboard, a keypad, a mouse, a touchpad, a touch-screen (described with respect to display interface 214), a multi-touch screen, a microphone for spoken command input (describe with respect to audio interface 216), and the like.

I/O processor 220 is generally employed to handle transactions and communications with peripheral devices such as mass storage, network, input devices, display, and the like, which couple computing device 200 with the external world. In small, low power computing devices, such as some mobile devices, functions of the I/O processor 220 may be integrated with CPU 204 to reduce hardware cost and complexity. In one embodiment, I/O processor 220 may the primary software interface with all other device and/or hardware interfaces, such as optical storage 202, hard disk 232, interfaces 226-228, display interface 214, audio interface 216, and input devices 218.

An electrical bus 222 internal to computing device 200 may be used to couple various other hardware components, such as CPU 204, memory module 206, I/O processor 220, and the like, to each other for transferring data, instructions, status, and other similar information.

Non-volatile memory 224 may include memory built into computing device 200, or portable storage medium, such as USB drives that may include PCM arrays, flash memory including NOR and NAND flash, pluggable hard drive, and the like. In one embodiment, portable storage medium may behave similarly to a disk drive. In another embodiment, portable storage medium may present an interface different than a disk drive, for example, a read-only interface used for loading/supplying data and/or software.

Various other interfaces 226-228 may include other electrical and/or optical interfaces for connecting to various hardware peripheral devices and networks, such as IEEE 1394 also known as FireWire, Universal Serial Bus (USB), Small Computer Serial Interface (SCSI), parallel printer interface, Universal Synchronous Asynchronous Receiver Transmitter (USART), Video Graphics Array (VGA), Super VGA (SVGA), HDMI (High Definition Multimedia Interface), and the like.

Network Interface Card (NIC) 230 may include circuitry for coupling computing device 200 to one or more networks, and is generally constructed for use with one or more communication protocols and technologies including, but not limited to, Global System for Mobile communication (GSM), code division multiple access (CDMA), time division multiple access (TDMA), user datagram protocol (UDP), transmission control protocol/Internet protocol (TCP/IP), SMS, general packet radio service (GPRS), WAP, ultra wide band (UWB), IEEE 802.16 Worldwide Interoperability for Microwave Access (WiMax), SIP/RTP, Bluetooth, Wi-Fi, Zigbee, UMTS, HSDPA, WCDMA, WEDGE, or any of a variety of other wired and/or wireless communication protocols.

Hard disk 232 is generally used as a mass storage device for computing device 200. In one embodiment, hard disk 232 may be a Ferro-magnetic stack of one or more disks forming a disk drive embedded in or coupled to computing device 200. In another embodiment, hard drive 232 may be implemented as a solid-state device configured to behave as a disk drive, such as a flash-based hard drive. In yet another embodiment, hard drive 232 may be a remote storage accessible over network interface 230 or another interface 226, but acting as a local hard drive. Those skilled in the art will appreciate that other technologies and configurations may be used to present a hard drive interface and functionality to computing device 200 without departing from the spirit of the present disclosure.

Power supply 234 provides power to computing device 200. A rechargeable or non-rechargeable battery may be used to provide power. The power may also be provided by an external power source, such as an AC adapter or a powered docking cradle that supplements and/or recharges a battery.

Transceiver 236 generally represents transmitter/receiver circuits for wired and/or wireless transmission and receipt of electronic data. Transceiver 236 may be a stand-alone module or be integrated with other modules, such as NIC 230. Transceiver 236 may be coupled with one or more antennas for wireless transmission of information.

Antenna 238 is generally used for wireless transmission of information, for example, in conjunction with transceiver 236, NIC 230, and/or GPS 242. Antenna 238 may represent one or more different antennas that may be coupled with different devices and tuned to different carrier frequencies configured to communicate using corresponding protocols and/or networks. Antenna 238 may be of various types, such as omni-directional, dipole, slot, helical, and the like.

Haptic interface 240 is configured to provide tactile feedback to a user of computing device 200. For example, the haptic interface may be employed to vibrate computing device 200, or an input device coupled to computing device 200, such as a game controller, in a particular way when an event occurs, such as hitting an object with a car in a video game.

Global Positioning System (GPS) unit 242 can determine the physical coordinates of computing device 200 on the surface of the Earth, which typically outputs a location as latitude and longitude values. GPS unit 242 can also employ other geo-positioning mechanisms, including, but not limited to, triangulation, assisted GPS (AGPS), E-OTD, CI, SAI, ETA, BSS or the like, to further determine the physical location of computing device 200 on the surface of the Earth. It is understood that under different conditions, GPS unit 242 can determine a physical location within millimeters for computing device 200. In other cases, the determined physical location may be less precise, such as within a meter or significantly greater distances. In one embodiment, however, a mobile device represented by computing device 200 may, through other components, provide other information that may be employed to determine a physical location of the device, including for example, a MAC address.

FIG. 3A shows an example sports headgear, in this case a helmet 300, including a data measurement and processing module 306 configured to measure attributes of an impact or a self-initiated movement and further including a video or still camera 312 (including lens 310). Sports helmet 300 includes head shield 304, face guard 308, and Data Measurement and Processing Module ("DMPM") 306.

In various embodiments, DMPM includes one or more sensors, such as accelerometers, and may include a processor, such as a microcontroller, configured to measure a dynamic characteristic, such as acceleration and/or deceleration, of the helmet due to impact or other force and process the measured data. DMPM may include one or more preset threshold values, such as values for acceleration (or deceleration), that when exceeded, the DMPM provides an indication or alarm such as a light, a sound, an electronic alert message, recording of an event in memory, and the like. In other embodiments, the DMPM may only include some of the above-mentioned components while the other components are separate but coupled, wirelessly or otherwise, with the DMPM. For example, the DMPM may include only an accelerometer and a threshold setting, while the processor and/or alarm may be a separate device, such as an LED or a beeper, coupled with the DMPM via wire or wirelessly. In some embodiments the DMPM may not have any threshold setting capabilities and continuously record impact characteristics of interest, such as accelerations.

Those skilled in the art will appreciate that the components and modules used in performing the data measurement and processing functions may be packaged, integrated, or coupled together in many different ways without departing from the spirit of the present disclosures.

Force of impact may be calculated based on the equation relating force to mass and acceleration: F=MA, where F is force, M is mass, and A is acceleration (or deceleration which is negative acceleration). A small device called an accelerometer may be used to measure the acceleration or deceleration of a body. The accelerometer device measures acceleration, for example by measuring a change in capacitance in a circuit in response to acceleration experienced by the device. The acceleration numbers may then be used to compute forces experienced if the mass of the player and/or the player part is known. Some accelerometers measure acceleration along one direction, while others are multi axial, for example 3-axis, devices which can measure acceleration in three orthogonal dimensions designated as X, Y, and Z dimensions. The acceleration along each of the three dimensions are measured and provided independently by the accelerometer. These three acceleration components may then be combined using vector calculus to obtain a resultant acceleration vector showing the total effective magnitude and final direction of the acceleration the body experiences.

In various embodiments, DMPM may include only an accelerometer and minimal circuitry with a settable hardware threshold for acceleration and an LED (Light Emitting Diode) light to indicate when the preset threshold has been exceeded. In these embodiments, the DMPM is a self-contained module which may be built into the helmet or be affixed to it via glue, screw, or other fasteners.

In other various embodiments, the DMPM may be more functional including a small circuit board having one or more accelerometers, a processor or programmable microcontroller, memory, a display device, and a communication module to transfer data to other local or remote computing devices, wirelessly or otherwise, as described above with respect to FIGS. 1 and 2.

In various embodiments, upon an impact or other sudden force and movement, which causes acceleration or deceleration of the body and the head, the accelerometers are calibrated and configured to measure acceleration of the helmet, and thus the head and the brain. The measured value may be saved in a memory or output from the accelerometer for further processing. In some embodiments, the processing may be as simple as comparing the measured acceleration value with a preset threshold and turning on an LED light or other similar indicator. In other embodiments, the processing may entail electronically reading the value by a processor via a data interface, storing the value, comparing it to previous values so measured, comparing to one or more thresholds, transmitting the original reading and/or other calculation to a remote host computer for still further processing, and the like.

In some embodiments, different algorithms may be executed on the DMPM processor or on the host processor to use multiple measured values and other calculated data to further analyze impact patterns, build a user profile, assess risk, provide recommendations, generate an exercise or action program for players or participants, and the like.

Other calculated data obtained from measured values include direction and magnitude of impact force, time of each impact, frequency of impacts, impact patterns in the form of fitted curves over other data points, and the like.

Once the measured values and other data are obtained and calculated, respectively, some or all of the results may be displayed on a display device, such as a computer screen, integrated, coupled with, or apart from the DMPM, along with the video of the particular scenes containing the impacts to which the measurements belong. In some embodiments, the display device may be a text and/or graphical and video display device capable of displaying more data in more forms. In still other embodiments, the display device may be that of the host system which receives data from the DMPM.

In some embodiments, DMPM is configured with personal information of a particular player who is using the helmet, such as the player's ID number, so that the data measured and calculated can be added to the profile of the particular player for future and further analysis. This way, an impact profile and habitual movements of the player may be accessed and studied side by side as part of an exercise evaluation and/or a medical diagnostic program if a medical condition occurs later which may be related to the impacts the player received previously.

In some embodiments, one or more thresholds may be set for different purposes. For example, a learning or preventive threshold may be set to different values for different players or for the same player, setting it lower for new or smaller players and higher for bigger or more experienced players. An alarm may be issued and/or measurement data may be saved, if a threshold is exceeded once or a predetermined number of times. Thus, in addition to setting a threshold, a threshold limit or a number of times that the threshold must be exceeded to set off an alarm may also be set or programmed for operation. Such learning threshold may be used to prevent injuries and also to learn about effects of multiple softer impacts in the long run.

Another type of threshold(s) which may be set is an indicator threshold which may set relatively higher than the preventive threshold to indicate an impact which may be too high and may cause head injury. If such indicator threshold(s) is exceeded, it may indicate that the impact was too high and some immediate medical investigation or action may be necessary to avoid or mitigate head injury. A threshold limit may be used with all kinds of thresholds including the indicator threshold.

Those skilled in the art will appreciate that other types of thresholds for other purposes may be set without departing from the spirit of the present disclosures. For example, DMPM may be deployed on the inner surface (closest to the user's body) of a protective clothing article, such as a helmet or a vest to measure the acceleration or force transmitted through the protective clothing article to test for the effectiveness of such article in protecting the user and reducing felt impact.

The threshold values set may represent other quantities than acceleration. For example, the threshold values may represent force, time duration, angle of impact (as determined from acceleration vectors), or any other quantity which may be calculated based on acceleration, time, position, sequence of events, frequency of events, and other variables. For example, a threshold may be set for occurrence of a particular event N number of times, where N is the frequency of the particular event. Similarly, a threshold or condition may be set for a particular sequence of events. An event may be any occurrence such as exceeding a threshold, receiving an impact on a particular side, and the like.

Figure 3B:
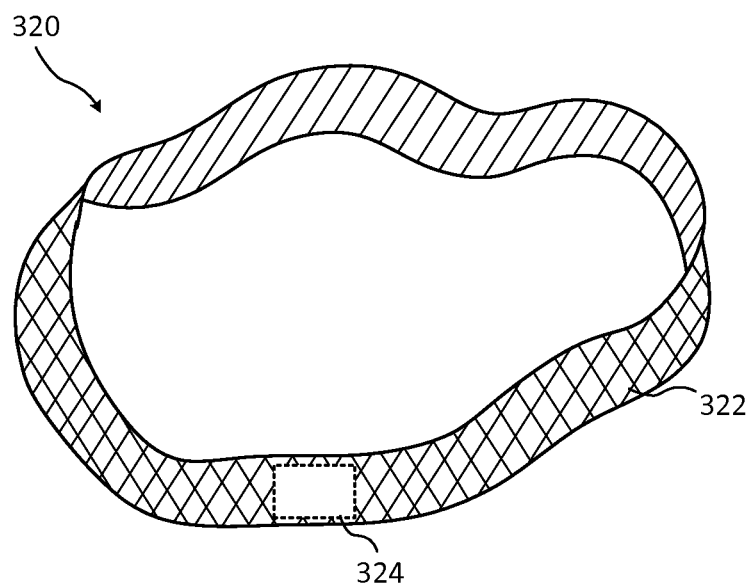
FIG. 3B shows an example headband including a data measurement and processing module configured to measure an impact acceleration/deceleration.

FIG. 3B shows an example headband 320 including a data measurement and processing module configured to measure an impact characteristics and attributes. In various embodiments, headband 320 includes an elastic or otherwise fastened member 322 with embedded DMPM unit 324.

In various embodiments, headband 320 does not protect the wearer form impact but only serves to measure impact attributes and dynamic characteristics experienced by the user's head due to impact or other sudden force. In various embodiments, headband member 322 may be an elastic band, a belt, an adhesive tape, and the like. Headband 320 may be embedded in or be implemented as other non-protective head covers, such as caps, hats, nets, shoes, and the like. In operation, headband 320 performs substantially the same functions as helmet 300 (FIG. 3A) with respect to DMPM, data measurements, data processing, and data transmission. A user may choose to wear such headband around her wrist or ankle and measure her self-initiated or impact-caused accelerations/decelerations and/or forces.

Figure 3C:
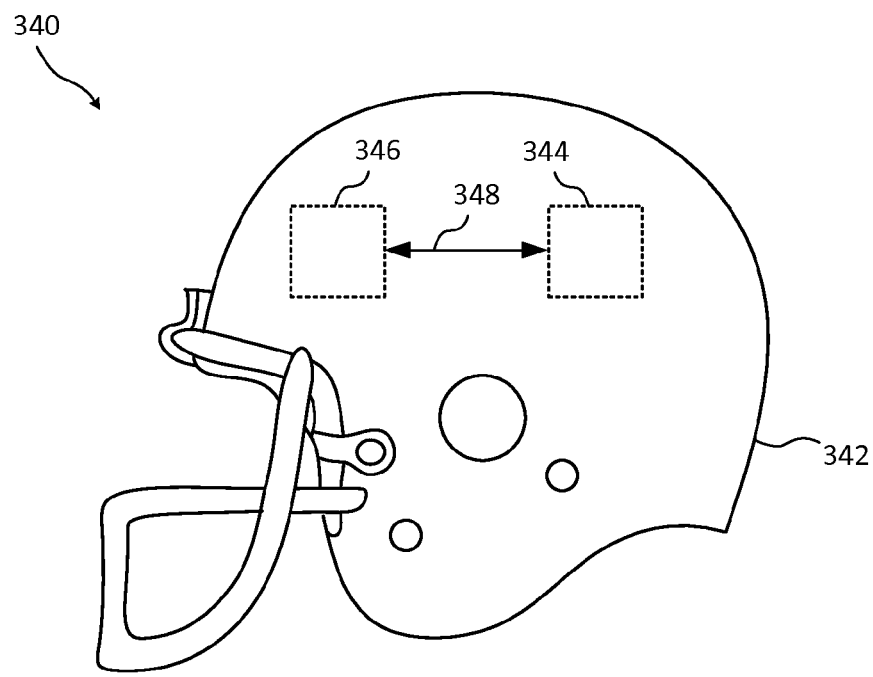
FIG. 3C shows an example sports helmet including multiple data measurement and processing modules configured to measure linear and rotational impact accelerations/decelerations.

FIG. 3C shows an example sports helmet 340 including multiple DMPM units configured to measure linear and rotational forces. In various embodiments, helmet 340 includes head shield 342, and two or more DMPM units 344 and 346 separated by a distance 348.

In various embodiments, helmet 340 substantially performs the same functions as helmet 300 (FIG. 3A), but has additional DMPM units to measure angular acceleration by combining acceleration data measured simultaneously by their respective accelerometers. Knowledge of the experienced rotational acceleration is useful because a head movement may substantially be a rotation in some direction around the neck or the body. Thus, knowing both the rectilinear acceleration and the angular acceleration of the head assist in performing a more complete analysis of forces experienced and the potential for injury.

In various embodiments, more than two DMPM units or accelerometers may be deployed to provide more readings for higher precision and also to provide error correction and fault tolerance in case one DMPM unit fails during operation.

Figure 3D:
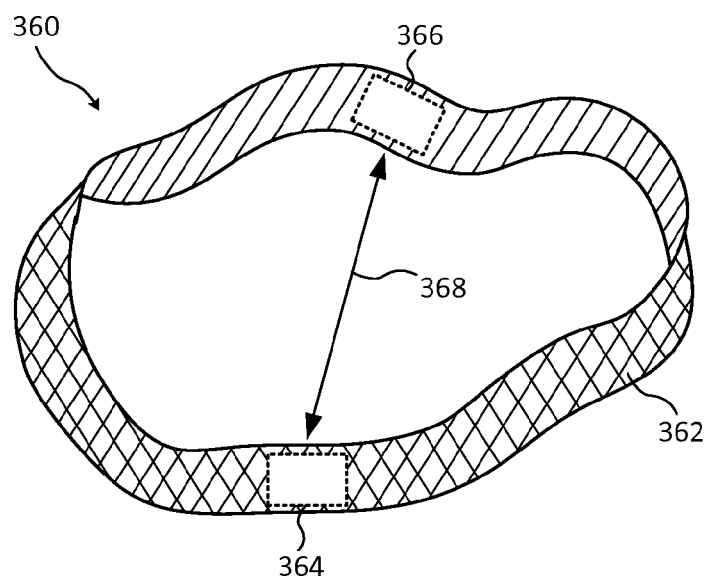
FIG. 3D shows an example headband including multiple data measurement and processing modules configured to measure linear and rotational impact accelerations/decelerations.

FIG. 3D shows an example headband 360 including multiple data measurement and processing modules configured to measure single or multiple impact forces. In various embodiments, headband 360 including elastic member 362 and DMPM units 364 and 366 separated by distance 368, is substantially similar to headband 340 (FIG. 3B) but with multiple DMPM units. The multiple DMPM units 364 and 366 operate substantially similarly to helmet 340 (FIG. 3C) in providing angular acceleration information. In some embodiments, one DMPM may have multiple sensors that are placed at different locations within or over the headband.

FIG. 4A shows an example American football encounter 400 which may result in concussion or trauma. This is a sport in which helmets are routinely used to protect players from head and face injuries during a tackle. During a physical encounter 400 players are protected by helmets 402 and 404. Using helmets such as helmets 300 and 340 shown in FIGS. 3A and 3C, respectively, incidents of head injury may be reduced in each game and also in the long run by studying the long term effects of impacts through the study of data collected by DMPM units and the corresponding scenes captured by video capturing device 406.

FIG. 4B shows an example martial art encounter 420 which may result in concussion or trauma. In martial arts, helmets are often not used due to their restrictive nature, however, lighter and less intrusive headbands may be used. In an example martial encounter 420 participants may wear headbands 422 and 424 to allow monitoring of impacts to the head or self-initiated head accelerations in conjunction with the associated scenes captured by camera 426.

In variable embodiments the DMPM may be any combination of a measurement device, a transmitter, a data storage, and a processor. In such embodiments the measurement data can be locally stored or be sent to a remote host computer along with an assigned data identifier such as a time-stamp, or be sent to a remote host computer where the computer saves the data in a manner that will be later correlatable to a particular captured video scene, or a combination thereof. The assigned data identifier may contain any information about the measurement data and the player whose movement characteristics are measured, along with other information such as time of the measurement and information about the particular exercise or event.

Correlation of Impact Scenes and Measured Data

In various embodiments, to conveniently correlate and associate a measured data with the video image of its impact scene, a time-based stamping of the measurement and video data, for example, is employed. In a time-based correlation, the DMPM logs the time of occurrence of an impact along with its measurements and/or calculations, and at the same time the video capturing device time-stamps frames or scenes of the captured activity, and/or assigns a scene identifier on a frame basis or scene basis. Such scene identifier may be correlated with the data identifier generated by the DMPM for the measured data to allow correlation between an event detected by the DMPM and the corresponding scene captured by the video camera including the detected event. Using the time-stamped video scenes and measurement data, it will be easy to retrieve the visual information related to any impact of interest. The time-stamps of the measurement data and the video of the corresponding activity may be based on absolute/actual times, such as the time of the day or the Greenwich Mean Time (GMT), or based on relative times, such as the elapsed time between the start of an activity and a desired impact, or the time between any other time reference and a desired point during the activity.

In various embodiments, DMPM and the video camera may be synchronized with each other using a synchronization signal and subsequently measure the time-lapses between the synchronized start-time and a target event. The synchronization may be manually performed by the user, for example, by pressing a designated button or done automatically by the DMPM and/or the video camera. The time synchronization of the DMPM and the video capturing device may also be with respect to each other or with respect to a third time reference.

In any embodiment, the time-based approach can be replaced by other means of associating a scene with the measured data. For example, each time an impact of certain characteristics is measured and/or calculated, an RF or another signal is sent by the DMPM to the video capturing device to stamp or otherwise mark the related scene, for example with a time-stamp or with a unique ID provided by the DMPM or with a unique ID generated by the video capturing device, etc. In other embodiments the video camera may constantly send scene related identifiers to the DMPM to be used for stamping the measured and/or calculated data. An identifier may contain any additional information such as information related to measurement data and the player whose movement characteristics are measured, along with other information such as time of the measurement and information about the particular exercise or event.

While specific circuitry may be employed to implement the disclosed embodiments, aspects of the invention can be implemented in a suitable computing environment. Although not required, aspects of the invention may be implemented as computer-executable instructions, such as routines executed by a general-purpose computer, e.g., a server computer, wireless device or personal computer. Those skilled in the relevant art will appreciate that aspects of the invention can be practiced with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics, set-top boxes, network PCs, mini-computers, mainframe computers, mobile devices, and the like. Indeed, the terms "computer," "host," and "host computer" are generally used interchangeably herein, and refer to any of the above devices and systems, as well as any data processor.

Downloadable or free software may be offered to those users who intend to utilize the advantages of the proposed methods. Aspects of the invention can be embodied in a special purpose computer or a data processor that is specifically programmed, configured, or constructed to perform one or more of the processes explained in detail herein. Aspects of the invention can also be practiced in distributed computing environments where tasks or modules are performed by remote processing devices, which are linked through a communications network, such as a Local Area Network (LAN), Wide Area Network (WAN), or the Internet. In a distributed computing environment, program modules may be located in both local and remote memory storage devices.

Aspects of the invention may also be stored or distributed on computer-readable media, including magnetically or optically readable computer discs, hard-wired or preprogrammed chips (e.g., EEPROM semiconductor chips), nanotechnology memory, or other data storage media. Indeed, computer implemented instructions, data structures, screen displays, and other data under aspects of the invention may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the invention reside on a server computer, while corresponding portions reside on a client computer such as a mobile or portable device, and thus, while certain hardware platforms are described herein, aspects of the invention are equally applicable to nodes on a network.

Changes can be made to the claimed invention in light of the above Detailed Description. While the above description details certain embodiments of the invention and describes the best mode contemplated, no matter how detailed the above appears in text, the claimed invention can be practiced in many ways. Details of the system may vary considerably in its implementation details, while still being encompassed by the claimed invention disclosed herein.

Particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the claimed invention to the specific embodiments disclosed in the specification, unless the above Detailed Description section explicitly defines such terms. Accordingly, the actual scope of the claimed invention encompasses not only the disclosed embodiments, but also all equivalent ways of practicing or implementing the claimed invention.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The above specification, examples, and data provide a complete description of the manufacture and use of the claimed invention. Since many embodiments of the claimed invention can be made without departing from the spirit and scope of the disclosure, the invention resides in the claims hereinafter appended. It is further understood that this disclosure is not limited to the disclosed embodiments, but is intended to cover various arrangements included within the spirit and scope of the broadest interpretation so as to encompass all such modifications and equivalent arrangements.

What is claimed is:

1. A device for measuring and processing a predefined out-of-bound characteristic of a user's movements and capturing video data corresponding to the user's movements, the device comprising:

a Data Measurement and Processing Module ("DMPM") coupled with a clothing article or gear configured to be worn on a body part of the user, the DMPM configured to measure the out-of-bound characteristic of movements of the body part of the user, if a preset threshold is exceeded by said measured movement characteristic, and further configured to process measurement data and to assign a data identifier to the measurement and/or to the processed data of each out-of-bound characteristic and configured to transmit an alert signal once the preset threshold is exceeded, wherein the assignment of data identifiers and the transmittal of alert signals are performed autonomously by the DMPM and without an external command signal sent to the DMPM; and a video camera configured to capture video scenes of the user's movements and configured to assign a scene identifier, upon receiving the alert signal from the DMPM, to the captured video scenes of the movements with out-of-bound characteristic, wherein the assigned data identifier of each out-of-bound characteristic is uniquely correlatable to the assigned scene identifier of the corresponding captured video scene, and wherein the video camera captures video scenes of the user's movement autonomously and without an external command signal sent to the video camera.

2. The device of claim 1, wherein the data identifiers and the scene identifiers include time-stamps.

3. The device of claim 1, further comprising a communication module configured to transmit information to a remote host computer.

4. The device of claim 1, wherein the DMPM includes an accelerometer for measuring an out-of-bound acceleration of the user's body part and a processor coupled with the accelerometer to process the measured acceleration.

5. The device of claim 1, wherein the video camera assigns the scene identifier to the captured video scene upon receiving an RF or an IR signal from the DMPM to do so.

6. The device of claim 1, wherein the preset thresholds are fixed, programmable, or a combination of fixed and programmable.

7. The device of claim 1, wherein the clothing article or gear is a helmet, a head-band, a wrist-band, an ankle-band, a sports gear, a hat, a cap, or a shoe.

8. The device of claim 1, wherein the video camera is configured to be attached to the user.

9. The device of claim 1, wherein the characteristic of the movements is at least one of speed, acceleration, force, energy, or momentum and wherein the processed data is at least one of formatted data, converted data, computed speed, computed acceleration, computed force, computed energy, or computed momentum.

10. A method of measuring and processing a predefined significant characteristic of a body part of a user's movements and capturing video data corresponding to the measured movements, the method comprising:

measuring the predefined significant characteristic of the movements of the body part of the user and if a preset threshold is exceeded by said predefine significant characteristic, processing the measurement data and assigning a data identifier to the measurement and/or the processed data of each significant characteristic and transmitting an out-of-bound announcement signal using a measurement and processing device ("DMPM") that is coupled with a clothing article or gear worn on a body part of the user, wherein the assignment of data identifiers and the transmittal of announcement signals are performed autonomously by the DMPM and without an external command signal sent to the DMPM; and capturing video scenes of the user's movements, using a video capturing device, and assigning a scene identifier to at least the captured video scenes of the movements with the predefined significant characteristic once the out-of-bound announcement signal is received, wherein the assigned data identifier is uniquely correlatable to the assigned scene identifier of the corresponding captured video scene, and wherein the video capturing of the user's movements are performed automatically by the video capturing device and without an external command signal sent to the video capturing device.

11. The method of claim 10, wherein the assigned data identifiers and assigned scene identifiers are time-based.

12. The method of claim 10, further comprising communicating information and control signals to and from a remote host computer.

13. The method of claim 10, wherein the measuring and processing includes measuring a significant acceleration of the user's body part and processing the measured acceleration.

14. The method of claim 10, wherein data identifiers and scene identifiers include absolute or relative time.

15. The method of claim 10, wherein the data identifier includes identification of the wearer of the clothing article or gear, information about the measurement data, time of measurement, or a particular exercise or event.

16. A method of measuring and processing a predefined attribute of a user's movements and correlating the measurements to captured video scenes of the user's movements, the method comprising:

measuring the predefined attribute of the movements of the user at least if a preset condition is met by said attribute, using a measurement device attached to the user by a clothing article or gear;

storing the measurement data in a storage device attached to the user or transmitting the data to a remote computer;

assigning data identifiers to the measurement data to uniquely identify measurement data related to each movement by which the preset condition of its predefined attribute is met;

capturing video scenes, by a video capturing device, of the user's movements; and assigning scene identifiers to the captured video scenes of the user's movements, to uniquely identify the captured video scenes such that each captured video scene can be associated with measurement data obtained from the movements within said scene, wherein the video capturing of the user's movements is performed autonomously by the video capturing device without an external command signal sent to the video capturing device.

17. The method of claim 16, further processing the measurement data by the measurement device attached to the user, by the remote computer, or by both.

18. The method of claim 16, wherein video scene capturing is performed by a video capturing device or a still camera.

19. The method of claim 18, wherein each measurement data identifier is based on an actual time of data measurement or is based on a relative time between a time reference and the time of the data measurement, and wherein each scene identifier is based on an actual time of scene capturing or is based on a relative time between a time reference and the time of the scene capturing.

20. The method of claim 16, wherein measurement data identifier and captured video scene identifier are time-based.

* * * * *